United States Patent [19]

Kanekiyo et al.

[11] Patent Number: 4,898,685
[45] Date of Patent: Feb. 6, 1990

[54] SURFACE ACTIVE COMPOUND

[75] Inventors: Takazumi Kanekiyo; Yukitoshi Akimoto; Miho Kubota; Koichi Fujita; Yasunori Koizumi, all of Mie, Japan

[73] Assignee: Mitsubishi Petrochemical Co., Ltd., Tokyo, Japan

[21] Appl. No.: 367,318

[22] Filed: Jun. 16, 1989

[30] Foreign Application Priority Data

Jul. 11, 1988 [JP] Japan ................... 62-172177

[51] Int. Cl.⁴ .................. B01F 17/12; C07C 143/24
[52] U.S. Cl. ........................ 252/353; 562/88
[58] Field of Search .................... 562/88; 252/353

[56] References Cited

U.S. PATENT DOCUMENTS 4,469,608 9/1984 Hinkamp ................ 252/353

OTHER PUBLICATIONS

Nishihara Chem. Abst. 98:160410k (1983).
Rugen et al. Chem. Abst. 96:7636c (1982).

Primary Examiner—Alan Siegel
Attorney, Agent, or Firm—Oblon, Spivak, McClelland, Maier & Neustadt

[57] ABSTRACT

An alkylbiphenyldisulfonate represented by formula:

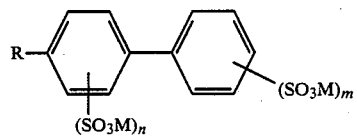

wherein R represents an alkyl group having from 10 to 15 carbon atoms; M represents an alkali metal atom; and m and n each represents 0, 1, or 2, and $m+n=2$. The alkylbiphenyldisulfonate exhibits excellent solubility in a concentrated aqueous electrolytic solution and, when used in an emulsion polymerization system, provides a polymer having a fine particle size and excellent stability.

9 Claims, 1 Drawing Sheet

SURFACE ACTIVE COMPOUND

FIELD OF THE INVENTION

This invention relates to a novel surface active compound and, more particularly, to an alkylbiphenyl disulfonate which has excellent solubility particularly in a highly concentrated aqueous electrolytic solution and provides, when used as an emulsifying agent in emulsion polymerization, a polymerization product having a fine particle size and excellent emulsion stability.

BACKGROUND OF THE INVENTION

Alkylbenzenesulfonates are currently widespread as surface active agent, but their solubility in concentrated aqueous electrolytic solution is limited. For example, in cleaning of a metallic surface with a combination of an aqueous alkali solution and a surface active agent to remove animal or vegetable oils, nonionic surface active agents have generally been employed.

Nonionic surface active agents, however, show weaker dispersing ability as compared with anionic surface active agents. Further, since they exhibit no surface activity at temperatures above their cloud point, the temperature range of application to made of them is so limited.

On the other hand, anionic surface active agents, e.g., alkylsulfates, and nonionic emulsifying agents, e.g., polyvinyl alcohol, have been used for radical emulsion polymerization of vinyl monomers, e.g., vinyl acetate. The emulsion polymerization product obtained according to these systems have relatively large particle sizes of from one to several microns so that it is insufficient in chemical stability and mechanical stability.

There is hence a tendency to use anionic surface active agents which exhibit satisfactory solubility in highly concentrated aqueous electrolytic solutions and improve emulsion stability, such as alkyldiphenyl ether disulfonates as disclosed in U.S. Pat. No. 3,127,441 and alkenylsuccinates. Although the alkyldiphenyl ether disulfonates are effective to produce an emulsion polymerization product having a fine particle size and excellent emulsion stability, they are still unsatisfactory in performance, relatively expensive, and considerably limited in application.

SUMMARY OF THE INVENTION

One object of this invention is to provide a surface active compound which has satisfactory solubility in a highly concentrated aqueous electrolytic solution.

Another object of this invention is to provide a surface active compound which exhibits excellent performance properties in emulsion polymerization of vinyl monomers to provide a polymerization product having a fine particle size and exhibiting satisfactory emulsion stability.

It has now been found that the above objects of this invention can be accomplished by an alkylbiphenyl disulfonate represented by formula (I):

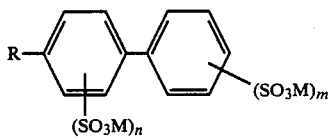

(I)

wherein R represents an alkyl group having from 10 to 15 carbon atoms; M represents an alkali metal cation; and m and n each represents 0, 1, or 2, and $m+n=2$.

DETAILED DESCRIPTION OF THE INVENTION

Figure 1:
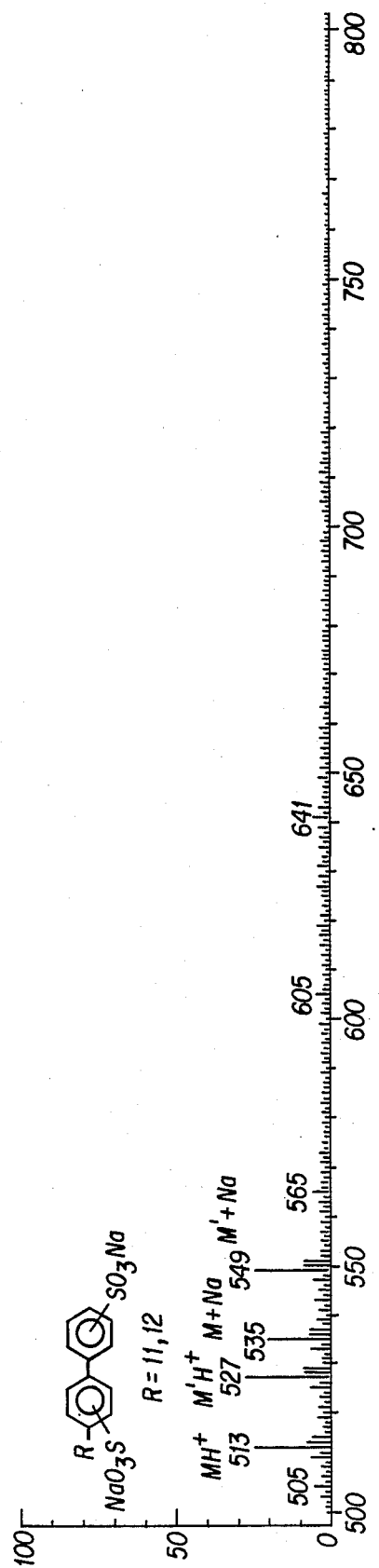
FIG. 1 is a mass spectrum of the disodium alkylbiphenyldisulfonate synthesized in Synthesis Example of this invention.

In formula (I), the alkyl group as represented by R includes decyl, undecyl, dodecyl, tridecyl, and tetradecyl groups which may be branched or straight-chain. The alkali metal forming a salt with the sulfonic acid includes sodium, potassium, and lithium.

From the standpoint of surface activity, solubility, and particle size and stability of emulsion polymers obtained, preferred of the compounds represented by formula (I) are sodium alkylbiphenyldisulfonates having from 11 to 12 carbon atoms in their alkyl moiety.

The position of the sulfo group is arbitrary as long as $m+n=2$. Included in the compounds of the present invention are those with one of the two benzene nuclei being substituted with two sulfo groups and those with each benzene nucleus being substituted with one sulfo group.

The compound of the present invention can be prepared by reacting biphenyl and an olefin in the presence of an alkylating catalyst to form a monoalkylbiphenyl, reacting the monoalkylbiphenyl with $SO_3$ at a molar ratio of 1:2, and neutralizing the resulting sulfonated product in an alkali metal hydroxide aqueous solution.

In more detail, the reaction between biphenyl and an olefin can be carried out by adding an alkylating catalyst, e.g., HF, dropwise to fused biphenyl and adding an olefin dropwise thereto at 50° to 80° C. while stirring. The reaction mixture is extracted, e.g., with cyclohexane, the HF layer removed, the oily layer neutralized and dehydrated, the solvent removed by distillation under reduced pressure, and the residue distilled to thereby isolate the monoalkylbiphenyl produced. The olefin which can be used in this reaction includes α-olefins having from 10 to 15 carbon atoms and internal olefins having from 10 to 15 carbon atoms. Mixtures of internal olefins are preferred in view of cheapness. The alkylating catalyst to be used include $AlBr_3$, $AlCl_3$, $GaCl_3$, $FeCl_3$, $SbCl_5$, $ZrCl_4$, $SnCl_4$, $BCl_3$, $BF_3$, $SbCl_3$, HF, and $H_2SO_4$, with HF being the most current in view of satisfactory reaction selectivity and inhibition of production of by-products.

Sulfonation of the monoalkylbiphenyl can be carried out by introducing 2 mols of $SO_3$ gas per mol of the alkylbiphenyl in an n-paraffin having from 5 to 8 carbon atoms or a chlorinated paraffin, e.g., dichloroethane, as a solvent while stirring at 5 to 10° C. $SO_3$ gas is usually used as diluted with an inert gas for reaction heat control. After introduction of a prescribed amount of $SO_3$ gas, the reaction system is aged for about 10 to 20 minutes. In order to inhibit formation of by-products, e.g., sulfones, due to dehydration condensation, water is added to the reaction mixture in an amount of not more than 10% by weight of the starting alkylbiphenyl. The solvent is then removed by distillation. The resulting sulfonated product is neutralized, e.g., with sodium hydroxide in an aqueous solution to obtain an aqueous solution of a disodium alkylbiphenyldisulfonate.

The compound of formula (I) may be used either as obtained in the form of an aqueous solution or, if desired, as isolated by water vaporization, recrystallization, and the like. The structure of the product can be confirmed by infrared absorption spectrum showing absorptions characteristic of a sulfonate at 1120 cm$^{-1}$ and 1200 cm$^{-1}$ and by mass spectrometry.

In cases where the compound of formula (I) is used in emulsion polymerization system, emulsion polymerization is usually conducted by stirring a mixture of a polymerizable monomer(s), e.g., styrene and acrylic esters, purified water, from 0.01 to 3% by weight of the compound of formula (I) as an emulsifying agent based on the monomer, and from 0.1 to 1% by weight of an initiator, e.g., persulfates, based on the monomer at a temperature of from room temperature to 95° C.

The present invention is now illustrated in greater detail by way of the following Example, but it should be understood that the present invention is not deemed to be limited thereto. In the description, all the percents are by weight unless otherwise indicated.

SYNTHESIS EXAMPLE

Synthesis of Sodium Alkylbiphenyldisulfonate

In a 10 l-volume corrosionproof reactor was charged 2,396 g of fused biphenyl. After cooling to 20° C. or less, 1,288 g of HF was added to the biphenyl. The temperature was elevated to 80° C., and the mixture was stirred at that temperature for 30 minutes, followed by cooling to 50° C. While the temperature being kept at 50° C., 824 g of a mixed internal olefin having from 11 to 12 carbon atoms was added to the reaction mixture over 30 minutes. After the addition, the stirring was continued for an additional period of 30 minutes to complete the reaction.

To the resulting mixture was added 3,220 g of cyclohexane, and the mixture was stirred for 5 minutes, followed by allowing to stand at 30° C. for 15 minutes. The lower HF layer was removed, and the oily layer was washed with water at 40° to 50° C., neutralized with a 5% aqueous solution of sodium hydroxide, and again washed with water. The oily layer was dehydrated using calcium chloride. The cylohexane was removed from the mixture by distillation under reduced pressure, and the residue was distilled to obtain 1,071 g of a monoalkylbiphenyl having a boiling point of 180° to 220° C./3 mmHg.

The product was found to have a purity of 99.9% by gas chromatography. The infrared spectrum of the product showed a sharp absorption peak assigned to paradisubstituted benzene at 830 cm$^{-1}$.

In 280 g of n-hexane was dissolved 50.4 g of the above-obtained 4-alkylbiphenyl (R=C$_{11}$—C$_{12}$), and the solution was put in a 1 l-volume four-necked flask. Then, SO$_3$ gas diluted to 10 vol % with nitrogen gas was introduced into the flask at a rate of 25 g/hr while stirring on an ice bath. One hour later, the amount of SO$_3$ reached 2 mols per mol of the starting compound, and, at this point, SO$_3$ introduction was stopped. After the reaction mixture was further stirred for 10 minutes for aging, 5 g of distilled water was added thereto. n-Hexane was removed by distillation by the use of a rotary evaporator to recover about 80 g of a residue. The residue was neutralized with 54 g of a 26% aqueous solution of sodium hydroxide to adjust to a pH of 8 to obtain 163 g of a disodium 4-alkylbiphenyldisulfonate (solid content: 42%).

The aqueous solution was evaporated to dryness, and the solid was recrystallized from a 1:1 (by volume) mixture of acetone and water to obtain an alkylbiphenyldisulfonate as a white powder.

Analysis by means of an infrared spectrometer (KBr method; JASCO A-302 Model) revealed that the spectrum showed antisymmetric and symmetric stretching vibrations due to SO$_3$Na at 1120 cm$^{-1}$ and 1200 cm$^{-1}$, respectively. The mass spectrum of the product obtained by means of a mass spectrometer (FAB/MS) under conditions (RT 0'18" FAB (Pos.) GC 0.0c BP: m/z 185.00 Scan# (3), and AMW=431.265 (361.692)) is shown in FIG. 1. The spectrum showed peaks due to parent ions formed by hydrogen ion addition to disodium undecylbiphenyl disulfonate at M/e=513, Na ion addition to disodium undecylbiphenyldisulfonate at 535, hydrogen ion addition to disodium dodecylbiphenyldisulfonate at 527, and Na ion addition to disodium dodecylbiphenyldisulfonate at 549.

Evaluation of Performance Properties:

(1) Solubility in Concentrated NaOH or HCl Aqueous Solution

The sodium alkylbiphenyldisulfonate aqueous solution as synthesized above was diluted with a 20% sodium hydroxide aqueous solution or 20% hydrochloric acid aqueous solution so as to have a salt concentration of 1%. Clarity of the resulting solution was examined in comparison with the corresponding solution prepared by using a 1% aqueous solution of sodium alkylbenzenesulfonate (LAS), and the results obtained are shown in Table 1 below. As is shown in Table 1, it was confirmed that the compound according to the present invention exhibits satisfactory solubility in a concentrated aqueous electrolytic solution.

TABLE 1

|  | 20% NaOH Aqueous Solution | 20% HCl Aqueous Solution |
| --- | --- | --- |
| LAS | white turbid | white turbid and phase separation |
| Sodium alkylbiphenyldisulfonate | clear | clear |

(2) Dispersing and Emulsifying Ability:

The sodium alkylbiphenyldisulfonate as synthesized above was evaluated for ability to disperse carbon black and ability to emulsifying n-dodecane according to the following test methods. For comparison, sodium laurylsulfate and sodium alkyldiphenyl ether disulfonate were similarly evaluated. The results obtained are shown in Table 2.

Test Method (1):

In a 100 ml-volume graduated measuring cylinder with ground stopper were charged 50 ml of a 0.2% aqueous solution of the test compound and 0.10 g of carbon black (produced by Tamagawa Carbon K.K.; C grade; dried at 105° C. for 3 hours), and the mixture was exposed to ultrasonic wave in an ultrasonic cleaner for 10 minutes to thereby disperse carbon black. After the dispersion was allowed to stand at 60° C. for 2 hours, the supernatant liquor was collected and the transmittance at 450 nm was measured by means of a spectrophotometer. The amount of dispersed carbon black (mg/100 ml) was obtained from the calibration curve.

Test Method (2):

In a 100 ml-volume graduated measuring cylinder with ground stopper were charged 20 ml of a 0.5% aqueous solution of the test compound and 20 ml of n-dodecane. The mixture was shaken 100 times for 1 minute and then allowed to stand at 25° C. for 1 hour. The volume of the emulsion layer (ml) was measured, and the emulsifying ability (%) was calculated therefrom according to equation:

Emulsifying ability (%) = Volume of Emulsion (ml)/40 (ml) × 100

EMULSION POLYMERIZATION EXAMPLE

In a 1 l-volume four-necked flask were charged 0.75 g of the sodium alkylbiphenyldisulfonate was obtained in Synthesis Example, 155 g of distilled water, and 15 g of vinyl acetate, and the mixture was heated to 50° C. on a warm water bath, followed by stirring at 500 rpm. Then, 1 ml of a potassium persulfate aqueous solution (0.45 g/10 ml) and 1 ml of an acidic sodium sulfite aqueous solution (0.45 g/10 ml) were added thereto, and subsequently, 60 g of vinyl acetate, 9 ml of the same potassium persulfate aqueous solution, and 9 ml of the same acidic sodium sulfite aqueous solution were added dropwise each at a constant rate over 1 hour by means of a microtube pump. After completion of the dropwise addition, the stirring was further continued at 50° C. for about 1 hour to obtain a latex.

The particle diameter of the resulting latex and stability of the latex on standing at room temperature for 1 month were determined according to the following methods. The results obtained are shown in Table 2.

Test Method (3):
The latex was appropriately diluted with distilled water, and the particle size of the latex was measured by the use of dynamic light-scattering photometer (DLS type, manufactured by Otsuka Electronics K.K.).

Test Method (4):
After allowing the latex to stand at room temperature for 1 month, a precipitate formed was separate by decantation, washed with water, air-dried, and weighed. The stability on standing was evaluated in terms of a weight percentage of the precipitate based on the total solid content of the latex.

and modifications can be made therein without departing from the spirit and scope thereof.

What is claimed is:

1. An alkylbiphenyldisulfonate represented by formula:

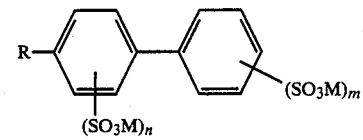

wherein R represents an alkyl group having from 10 to 15 carbon atoms; M represents an alkali metal atom; and m and n each represents 0, 1 or 2, and $m+n=2$.

2. An alkylbiphenyldisulfonate as claimed in claim 1, wherein R represents an alkyl group having from 11 to 12 carbon atoms.

3. An alkylbiphenyldisulfonate as claimed in claim 1, wherein M is sodium.

4. A surface active agent comprising an alkylbiphenylsulfonate represented by formula:

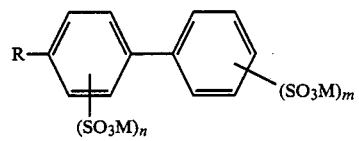

wherein R represents an alkyl group having from 10 to 15 carbon atoms; M represents an alkali metal atom; and m and n each represents 0, 1 or 2, and $m+n=2$, as an active component.

5. A surface active agent as claimed in claim 4, wherein R represents an alkyl group having from 11 carbon atoms.

6. A surface active agent as claimed in claim 4, wherein M is sodium.

7. A surface active agent for use in emulsion polymerization represented by formula:

TABLE 2

| Surface Active Compound | Dispersing Ability (mg/100 ml) | Emulsifying Ability (%) | Emulsion Polymerization | | Remarks |
| --- | --- | --- | --- | --- | --- |
| | | | Particle Size (μm) | Stability (%) | |
| 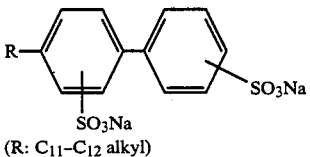 (R: C₁₁–C₁₂ alkyl) | 49 | 43 | 0.12 | 2.5 | This invention |
| Sodium laurylsulfate | 32 | 48 | 1.5 | 85.0 | Comparison |
| 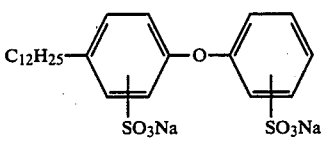 | 49 | 33 | 0.18 | 8.9 | Comparison |

While the invention has been described in detail and with reference to specific embodiments thereof, it will be apparent to one skilled in the art that various changes

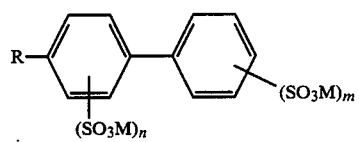
wherein R represents an alkyl group having from 10 to 15 carbon atoms; M represents an alkali metal atom; and m and n each represents 0, 1 or 2, and m+n=2.
8. A surface active agent as claimed in claim 7, wherein R represents an alkyl group having from 11 to 12 carbon atoms.
9. A surface active agent as claimed in claim 7, wherein M is sodium.
* * * * *